United States Patent
Chehab et al.

[19]
[11] Patent Number: 6,132,744
[45] Date of Patent: Oct. 17, 2000

[54] TALCUM POWDER COMPOSITION

[75] Inventors: Mohamad Nabil Chehab, Mumbai; Prashant Micky Puri, New Bombay; Pushker Sona, Mumbai, all of India

[73] Assignee: Unilever Home & Personal Care USA, division of Conopco, Inc., Greenwich, Conn.

[21] Appl. No.: 09/323,633

[22] Filed: Jun. 1, 1999

[30] Foreign Application Priority Data

Jun. 1, 1998 [IN] India ................... 333/BOM/98
Jul. 30, 1998 [GB] United Kingdom ............ 9816680

[51] Int. Cl.[7] .................. A61K 7/32; A61K 6/00; A61K 9/14; A61K 9/16; A01N 59/06
[52] U.S. Cl. .................. 424/401; 424/65; 424/489; 424/490; 424/683
[58] Field of Search .................. 424/357, 401, 424/489; 106/481, 490

[56] References Cited

U.S. PATENT DOCUMENTS

| | | |
|---|---|---|
| 4,000,317 | 12/1976 | Menda et al. . |
| 4,375,373 | 3/1983 | Abe et al. ............... 106/308 B |
| 5,122,418 | 6/1992 | Nakane et al. ............ 424/401 |
| 5,683,706 | 11/1997 | LaFleur et al. . |
| 5,738,718 | 4/1998 | Mori et al. ............... 106/481 |
| 5,827,507 | 10/1998 | Oshima et al. ............ 424/59 |

FOREIGN PATENT DOCUMENTS

| | | |
|---|---|---|
| 0 355 521 | 2/1990 | European Pat. Off. . |
| 0 581 651 | 2/1994 | European Pat. Off. . |
| 1 380 361 | 1/1975 | United Kingdom . |

*Primary Examiner*—Thurman K. Page
*Assistant Examiner*—Susan Tran
*Attorney, Agent, or Firm*—Milton L. Honig

[57] ABSTRACT

This invention relates to a synergistic combination of porous material such as metal silicates, silica, metal hydroxycarbonates, metal hydroxides, metal carbonates, metal aluminates with talc for use in talcum powders, deodorants, perfumery and other like cosmetic formulations and method for the manufacture of the same.

9 Claims, 6 Drawing Sheets

FIG. 1

FIG. 2A

SEM PHOTOGRAPHS OF TALC COATED SILICA (AT DIFFERENT TALC/$SiO_2$ RATIO)

FIG. 2B

SEM PHOTOGRAPHS OF TALC COATED SILICA (AT DIFFERENT TALC/SiO$_2$ RATIO)

FIG. 2C

SEM PHOTOGRAPHS OF TALC COATED SILICA (AT DIFFERENT TALC/$SiO_2$ RATIO)

FIG. 3

FIG. 4

TALCUM POWDER COMPOSITION

This invention relates to a synergistic combination of porous material such as metal silicates, silica, metal hydroxycarbonates, metal hydroxides, metal carbonates, metal aluminates with talc for use in talcum powders, deodorants, perfumery and other like cosmetic formulations and method for the manufacture of the same.

BACKGROUND AND PRIOR ART

Talc, $Mg_3Si_4(OH)_2$, is a natural mineral, with a sheet silicate structure. It has a platy morphology and is oleophilic/hydrophobic being wettable by oil rather than water. Talc provides good lubricity or slip and has acceptable fragrance retention. Known talcum powder formulations vary in complexity from merely talc and perfume to those having numerous components, especially in some products directed towards specific use.

It is found that the lubricity of talc is affected by repeated exposure to moisture, constant wetting and due to the formation of a thin layer of perfume molecules on the surface of talc platelets which induces stickiness. This causes a morphological change of the talc from a platy morphology to aggregates or globule formation which retard the flow property, hamper the spreadability (surface coverage) and may also be responsible for retarding the release/impact of perfume. This effect becomes increasingly acute for talcum powders formulated with other additives such as calcium carbonate, zinc stearate etc., and on increasing the perfume dosages in the formulation. Traditionally talcum powder manufacturers have been using super adsorbers such as cross linked carbomethyl cellulose and starch based derivatives in an attempt to overcome the aforementioned problems. However, these additives are not found to demonstrate significant improvement over talcum powders formulated without such super adsorbers.

U.S. Pat. No. 4,000,317 discloses the use of pyrogenic silica of spherical shape and very small particle size for adsorption of sebum, the oily material secreted by the sebaceous glands on the human face. However the said patent does not provide for any modification directed to improvement in talc properties for use in skin formulations and the like.

U.S. Pat. No. 5,683,706 discloses powder compositions containing high levels of talc, low levels of titanium dioxide and a sebum absorbing material to provide compositions having improved skin coverage, uniformity and duration of wear. However, the said patent also does not disclose or teach for improvement and/or modification in talc properties to achieve combination of desired beneficial effects in talc formulations for cosmetic and like applications. Moreover talc and sebaceous absorbing material used in the said patent would phase separate on account of bulk density and particle size distribution differences affecting talc benefit properties in the formulation.

It is found that talc as used for talcum powder has markedly inferior moisture absorbency. This further decreases due to the hydrophobic effect of perfume when it is sprayed on talc. Talc as such is a poor vehicle for retaining perfume. As such talc cannot be used for delivering deodorancy benefits.

It is thus an objective of the present invention to provide talc in a form whereby its lubricating (free flowing), moisture adsorption capacity, oil retention capacity, fragrance retention properties etc. are improved for use in various cosmetic and like applications.

Another object of the present invention is to provide a process for the manufacture of talc at least partly coated with porous material such as herein described, which provides talc having improved lubricating, moisture adsorption capacity, oil retention capacity, fragrance retention properties etc. for use in various cosmetic and like formulations.

Yet another object of the present invention is to provide a synergistic combination of talc coated and/or precipitated with porous material such as herein described which would have improved lubricating, moisture adsorption capacity, oil retention capacity, perfume retention capacity and thus suitable for use in various cosmetic formulations such as talcum powder, deodorant, deo-talc and the like.

Yet a further object of the present invention is directed to provide for synergistic talcum powder formulation comprising talc coated with porous material such as herein described.

SUMMARY OF INVENTION

Thus according to one aspect of the present invention there is provided a cosmetic talc-containing product wherein the talc is at least partially coated with a porous material selected from the group comprising metal silicates, silica, metal hydroxycarbonates, metal hydroxides, metal carbonates and/or metal aluminates, and wherein the cosmetic product is selected from the group comprising talcum powder, deodorant or a skin care cream/lotion or gel.

The talc coated with porous material selected from the group comprising metal silicates, silica, metal hydroxycarbonates, metal hydroxides, metal carbonates, and/or metal aluminates for use in the present invention may be prepared by:

i) wetting talc with a solution suitable to deliver said porous material;

ii) acidifying the wetted talc to precipitate said porous material; followed by iii) washing and drying; or by i) providing an aqueous solution of said talc;

ii) adding to said talc solution an acid solution and a solution suitable to deliver said porous material; followed by iii) filtering, washing and drying In this manner the porous material advantageously coats/deposits onto talc in situ.

In the above disclosed processes, the solution suitable for delivering said porous material comprises silicates, aluminates, hydroxides, carbonates and hydroxycarbonates of alkali metal and/or alkaline earth metal and/or transitional metals or mixtures of these. Preferably the alkali metals comprise sodium, potassium, said alkali earth metals comprise calcium, magnesium and said transitional metals comprise aluminium and zinc. In particular, the porous material used is selected from metal silicates, silica, metal hydroxycarbonates, metal hydroxides, metal carbonates, metal aluminates.

The acid suitable for use in the above disclosed processes can be any suitable organic and/or inorganic acid. Preferably, chloro acetic acid, sulphuric acid, hydrochloric acid, formic acid, stearic acid and alum are used. The selection of the acid used is based upon the desired hydrophobicity and/or hydrophilicity of the porous material coat/precipitate on the talc which in turn is dependant upon the desired end use/application of the coated talc. For example, typically the acids which are useful for generating hydrophillic porous material are mineral and inorganic acid such as sulphuric, hydrochloric, nitric acid etc, and the acids which are useful for generating hydrophobic porous material include halo-organic acids (e.g. chloroacetic acid) or fatty acids (e.g. stearic acids).

A further alternative process for manufacture of talc coated with porous material selected from the group comprising metal silicates, silica, metal hydroxycarbonates, metal hydroxides, metal carbonates and/or metal aluminates, comprises the steps of:

i) adding talc to a gel solution of said porous material;
ii) blending the talc and gel solution in a mixer; followed by
iii) drying Optionally, in the above process a further subsequent step of milling the dried porous material coated talc is provided to suit specific end uses.

The gel solution may be prepared in any conventional manner, for example, a dilute metal silicate solution may be converted into a gel solution of silica by acidification.

Surprisingly, talc which is at least partly coated with precipitated porous material as hereinbefore described has improved flowability, moisture/oil retention capability, perfume retention capacity and similar beneficial properties. Such a talc is obtainable by the processes of described above.

In accordance with a further aspect of the invention there is provided the use of talc in a cosmetic product wherein the talc is at least partially coated with a porous material selected from the group comprising metal silicates, silica, metal hydroxycarbonates, metal hydroxides, metal carbonates and/or metal aluminates, for the purposes of improving at least one property of the product selected from the group comprising perfume adsorption, stabilisation and retention, moisture absorption, deodorancy delivery, lubricity and free-flowability.

Preferably, the cosmetic product in which the talc is used is selected from the group comprising talcum powder, deodorant or skin care cream/lotion or gel.

In such a cosmetic product the talc may consist solely of talc coated and/or precipitated with the porous material. Alternatively the talc may be provided as a combination of conventional talc and talc which has been coated and/or precipitated with the porous material. Preferably the talc coated and/or precipitated with porous material in such cosmetic products is present in an amount of 5 to 20% by weight of the total talc in the formulation. Preferably the talc coated and/or precipitated with porous material may be used in an amount of 8 to 15% and most preferably 10 to 12.5% by weight of the composition of the cosmetic product, such as a talcum powder composition.

Preferably the porous material coated talc is dosed in the appropriate sequence in the manufacturing process of the cosmetic product to maximise the retention of the perfume and prevent losses during preparation.

In a particularly preferred embodiment, the porous material is silica.

The details of the invention, its objects and advantages will be more apparent from the ensuing description made with relation to non-limiting exemplary embodiments of the invention.

EXAMPLE 1

Process for manufacture of silica coated talc in accordance with the invention:
Raw Material used
  Talc: Conventional talc used in talcum powder.
Sodium silicate
  Composition $Na_2O$ 9.0%; $SiO_2$ 29.0%; $H_2O$ 62%
  Specific gravity 1.4

Sulfuric Acid
  Concentration 98%
  Specific gravity 1.835
Chloro Acetic Acid
  Hydrated chloro acetic acid, soluble in water.
Preparation of Solution
Dilute Sodium Silicate To 420 g Sodium Silicate, 220 g of water was added and stirred for 40 min. at room temperature. The specific gravity measured was 1.2.

Dilute Sulfuric Acid

To 314 g water, 64 g sulfuric acid was added slowly with stirring. The specific gravity of dilute acid was measured to be 1.12.

Chloro-Acetic Acid

15–20 gm dissolved in 56 ml of dilute sulfuric acid.

Process

The following process was carried out:

a) wetting of talc with the dilute sodium silicate solution is performed in the following manner: 200–800 g, preferably 480 g of talc is added to a pool of 1200–2000 g of water, preferably 1500 g of water. 7–10 g of the dilute solution silicate solution is introduced. A second dosage of the silicate solution (250–800 g, preferably 640 g) is dosed into the pool simultaneously with 250–450 g preferably 320 g of dilute sulfuric acid. Subsequently 35–75 g, preferably 56 g of the chloro-acetic acid solution is added to the pool.

b) dosing 1400–1500 g water to the reactor.

c) heating pool to 95–98° C.

d) mixing using overhead mixer.

e) adding 480 g of talc to pool and stir for 10 minutes.

f) adding 10 g dilute sodium silicate to pool (silicate) so as to make the solution alkaline (initial pH 10). Mix for 10 minutes.

g) simultaneously dosing silicate II (640 g at the rate of 29.7 g/min.) and Acid I (320 g at a rate of 15 g/min.). Maintaining temperature 95–98° C.

h) dosing acid II (56 g) at a rate of 5.6 g/min. until the pH 4 is attained.

i) continuing stirring for 5 minutes.

j) filtering the solution Wash the substrate with water (50–70° C.) until free of sulfate.

k) drying at 120° C.

l) wet cake is weighed 1862 g along with wt. of dried material 610 g, and m) milling the sample to break agglomerates.

Characteristics of talc coated with silica vis-a-vis talc and silica per se were studied Talc, $SiO_2$ and talc according to the present invention coated with Silica at 20% $SiO_2$ loading is compared in Tables 1 and 2 hereunder. Loading refers to the amount of silica coated talc as a percentage of total talc in the formulation. Thus "20% loading" means that 20% by weight of the total talc is talc coated with silica.

TABLE 1

Raw Material Properties

| PARAMETERS | $SiO_2$ (100%) | TALC (100%) | TALC 20% BEING COATED WITH $SiO_2$ HYDROPHILIC | TALC, 20% BEING COATED WITH $SiO_2$ HYDROPHOBIC |
|---|---|---|---|---|
| *ABD, g/cc | 0.1 | 0.43 | 0.3 | 0.41 |
| **TBD, g/cc | 0.13 | 0.60 | 0.35 | 0.49 |
| Moisture Content, 105° C. | 8.5 | 0.1 | 1.5 | 1.3 |

*ABD refers to "average bulk density"
**TBD refers to "tapped bulk density"

TABLE 2

Test results illustrating oil absorption value (OAV), Water absorption value (WAV), Surface Area, Perfume adsorption value

| PARAMETERS | $SiO_2$ (100%) | TALC (100%) | TALC 20% BEING COATED WITH $SiO_2$ HYDROPHILIC | TALC, 20% BEING COATED WITH $SiO_2$ HYDROPHOBIC |
|---|---|---|---|---|
| OAV, g/100 g | 250 | 70 | 95 | 114 |
| WAV, g/100 g | 250 | 55 | 98 | 78 |
| Surface Area | 180 | 10 | 67 | 72 |
| Denim Perfume Adsorption Value, g/100 g | 250 | 54.7 | 101 | 115 |
| WAV after 1.2% Perfume adsorption | 246 | 43 | 93 | 75 |

The WAV, OAV and Perfume adsorption value increases on coating talc with silica to form polymorphs.

Figure 1:
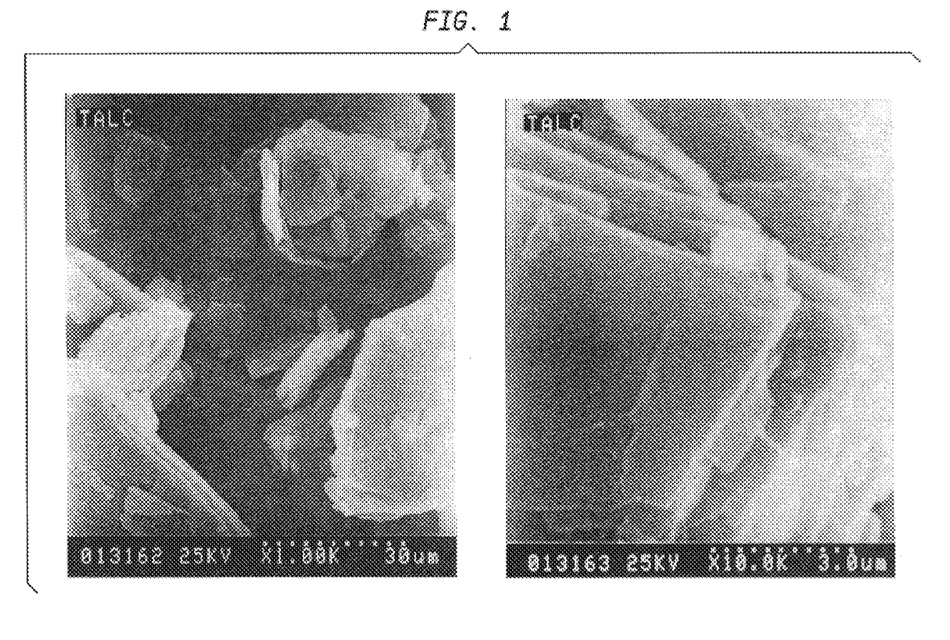

Morphology and particle size of modified talc (silica coated) in accordance with the invention with talc were analysed as described below:

The morphology and particle size were analyzed by scanning electron microscopy. The Talc platelets are sharp, platelet like and laminar in nature (FIG. 1). The individual talc laminae are held together to form particulates which are about 0.05 to 0.09 mm in dimensions. The surface of talc particles are smooth without growth or nucleating sites.

Figure 2A:
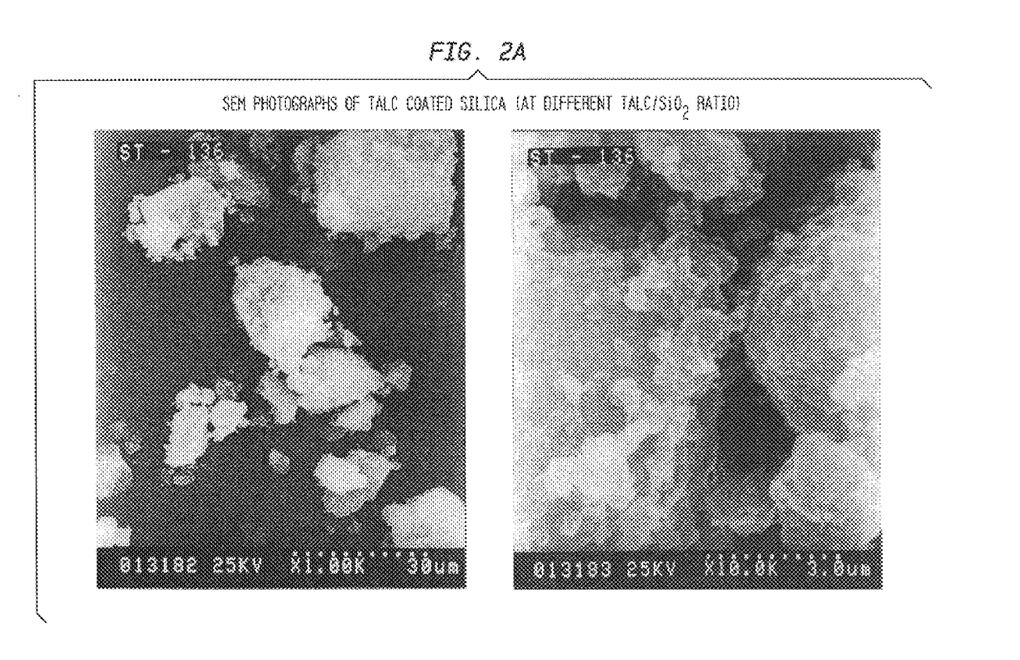
Figure 2B:
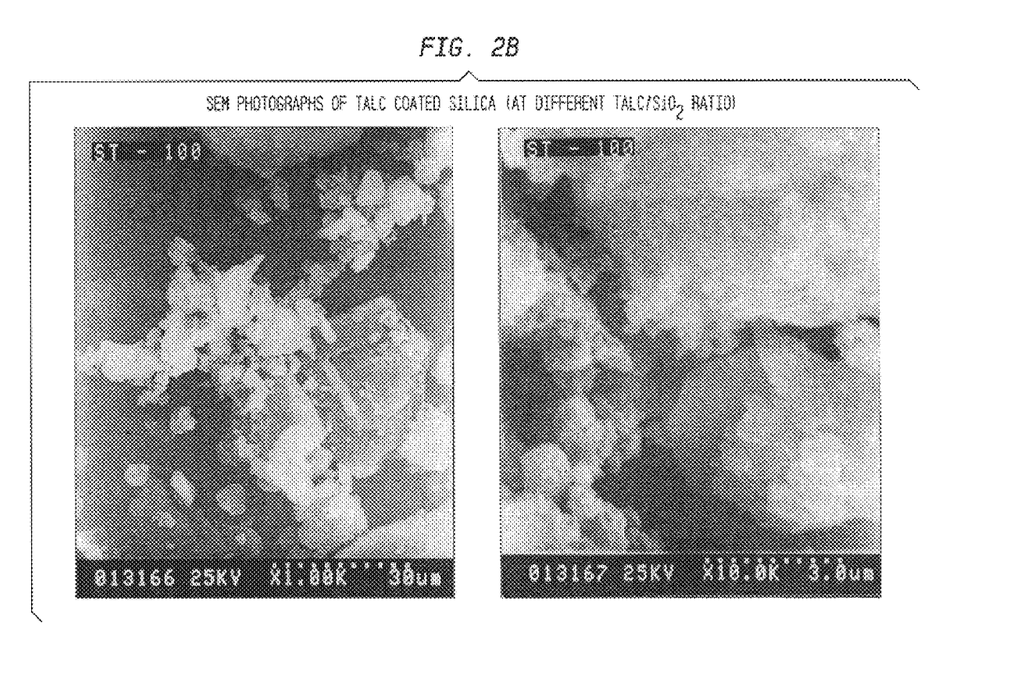
Figure 2C:
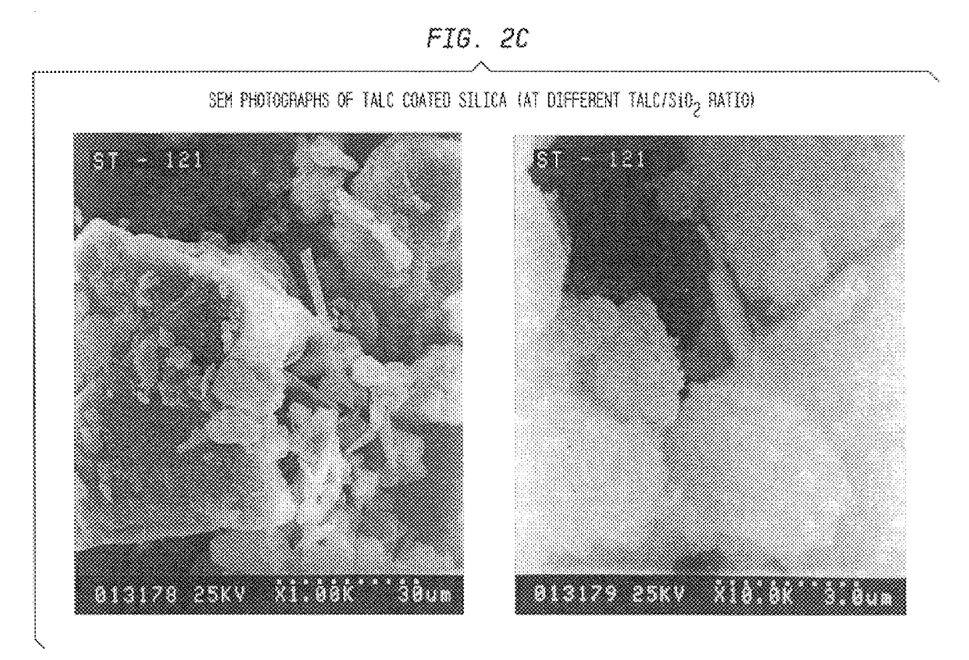

After aqueous alkali treatment, co-precipitation of silica, washing, filtration and drying the individual talc laminae in accordance with the present invention appear to have separated and the particles have fragmented. Three different samples are shown at two different magnifications in the FIG. 2.

The surface is no longer smooth and appears to have a growth of silica deposited on it. The particle size is in the range of about 0.01–0.03 mm in dimensions. The talc coated silica particulate are interdispersed with silica particulate of 3 to 6 microns. The amount of amorphous silica is dependent on the ratio of talc to sodium silicate taken during precipitation. It is clearly seen from the micrographs that silica gets deposited on the talc surface.

Figure 3:
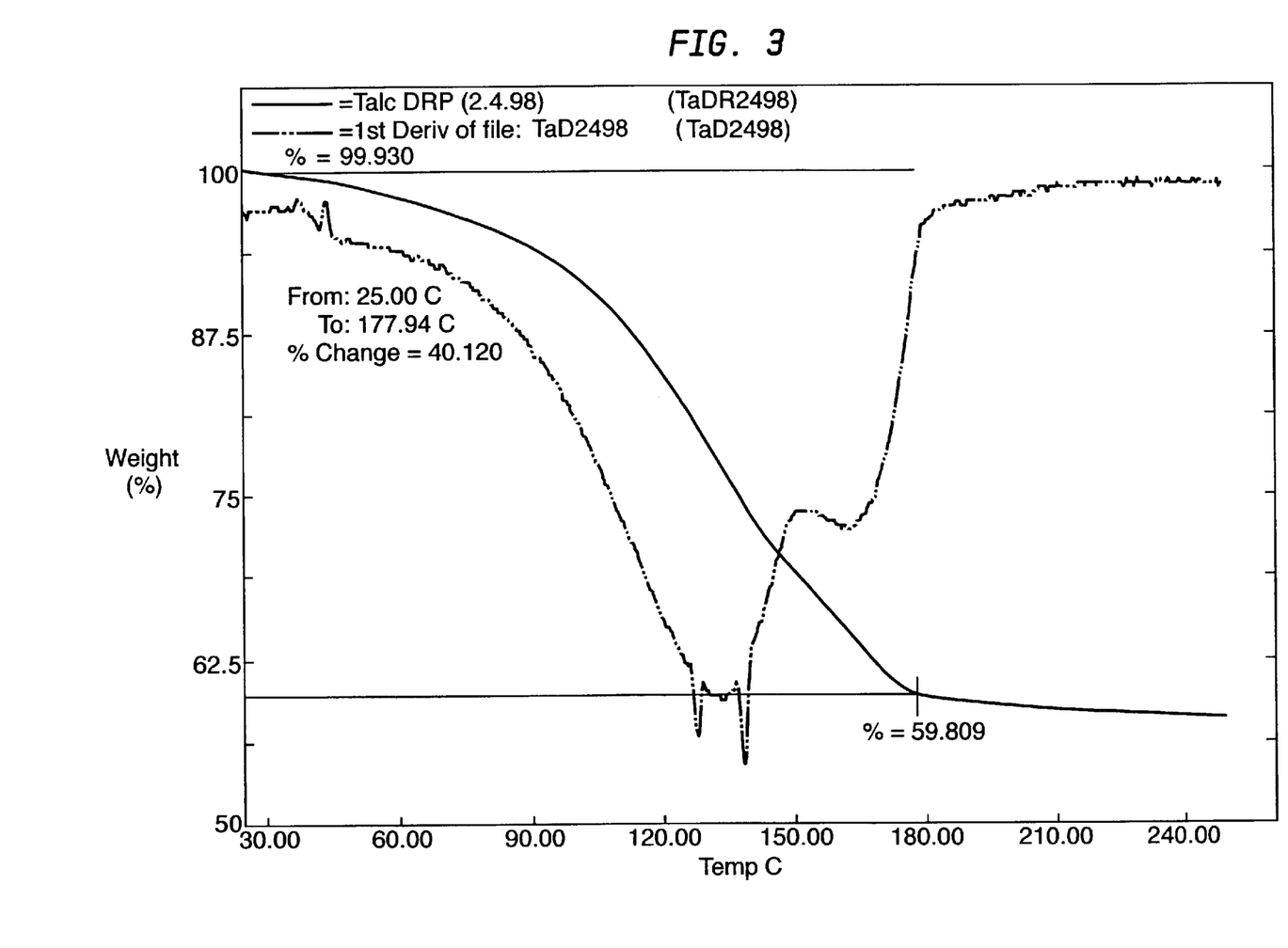
Figure 4:
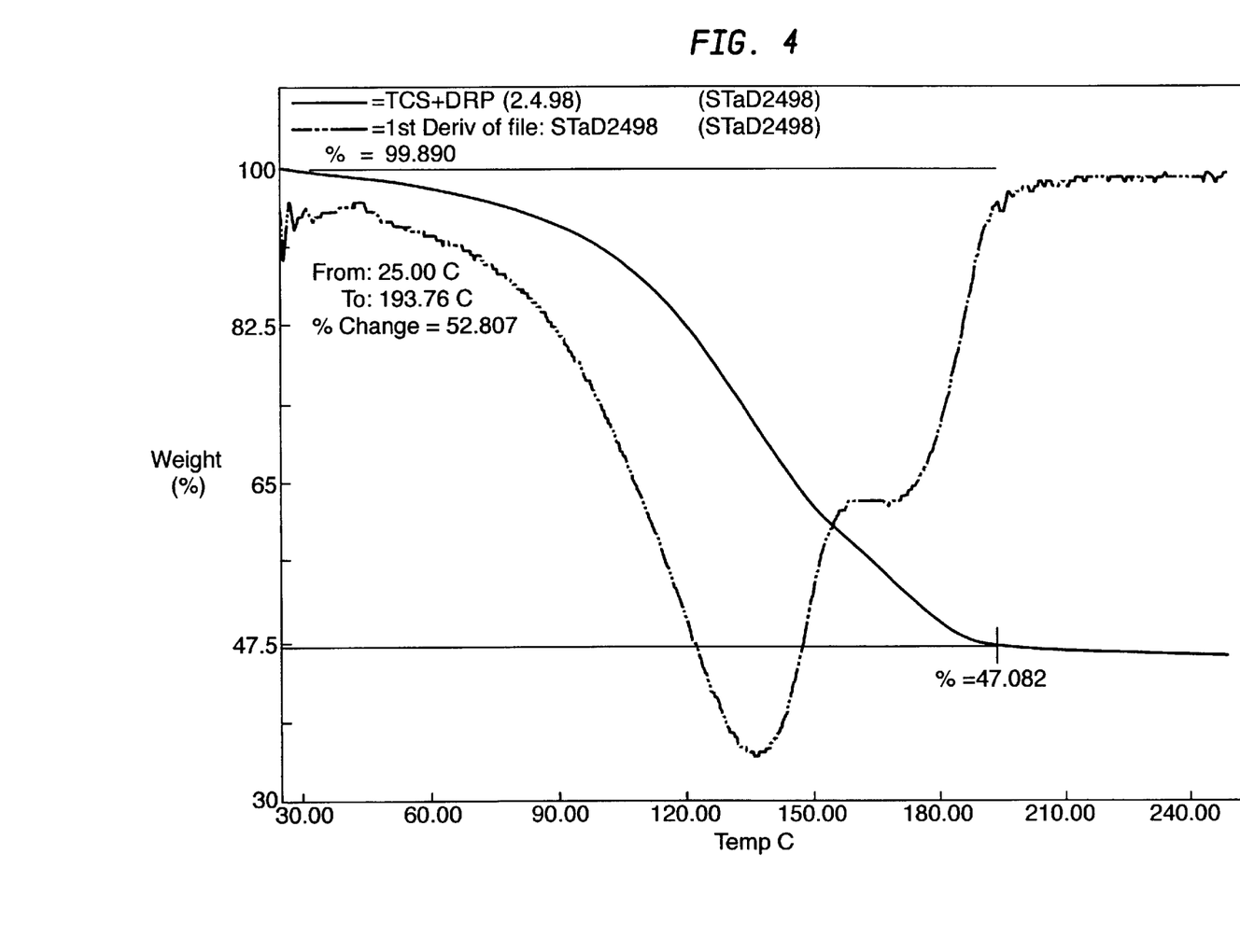

Perfume adsorption capacity of talc coated with $SiO_2$ vis-a-vis talc was studied by thermogravimetry as detailed hereunder:

Perfume adsorption capacity was determined for talc and talc coated silica by the ASTM rub out method. Denim perfume was used as the medium in this example. Talc showed a capacity of 54 g/100 g compared to 101 g/100 g of modified talc in accordance with the present invention. The nature of adsorption and the desorption temperature were investigated by subjecting the above two samples, after an equilibration period of 2 days, to thermogravimetric measurements. The TGA profiles are shown in the attached FIGS. 3 and 4 respectively.

The perfume appears to have two components, one which has a lower adsorption property which desorbs at 125–130° C. and the other which is more strongly adsorbed which requires a higher temperature of about 175–180° C. for desorption. This behavior is similar for both kind of substrates, suggesting that the perfume interaction/stabilization has not under gone any change in its nature. To investigate the amount of perfume retained and to characterize the nature of perfume through Head Space GC measurements both samples were loaded with 54% denim perfume by the ASTM rub-out method. The amount of perfume retained on the two substrates are compared below in Table 3:

TABLE 3

| Parameter | Talc | Talc coated with $SiO_2$ |
|---|---|---|
| % Perfume Absorption Value, g/100 g | 54 | 54 |
| After equilibration, % Wt Loss by TGA | 40 | 52 |
| Perfume Loss | 14 | 2 |
| % Perfume Loss | 25.9 | 3.7 |

The above results show that the talc with silica coating have extremely high perfume carrying and holding capacity resulting in lower loss of perfume.

Head Space GC Measurements were next studied as detailed hereunder:

The equilibrated samples were taken in equivalent amounts and sealed in head space vials and kept at 40° C. overnight. The sealed vial was placed into the sample carriage of the HS-100 head space sampler. Fixed aliquot of the head space was then automatically injected into the detector. After the detection, the vials were opened up and after 5 minutes resealed, equilibrated and resubjected for HSGC measurements. The results are given below in Table 4:

TABLE 4

| PARAMETER | TALC | TALC COATED SILICA |
|---|---|---|
| Total Area | 108732 | 127089 |
| Re-equilibrated sample | 84199 | 110688 |

The results show that talc particles coated with silica have a better perfume retention property. The elution time for each peak matched with the pure standard perfume for both samples. No suppression or new peak intensities were detected, indicating perfume compatibility.

The efficacy of the silica coated/precipitated talc in talcum powder formulations was next studied and for the purpose studies were carried out at 10% incorporation of talc—silica polymorphs in talcum powder formulations (i.e. 10% loading). A conventional talcum powder formulation (Example 2) was studied vis-a-vis two types of talc—silica polymorphs (Examples 3 and 4) of the present invention as per the formulations details hereunder in Table 5:

TABLE 5

| Material | Example 2 | Example 3 | Example 4 |
| --- | --- | --- | --- |
| Talc | 95.35 | 85.35 | 85.35 |
| CaCO3 | 2.0 | 2.0 | 2.0 |
| Zinc Stearate | 1.0 | 1.0 | 1.0 |
| Perfume | 1.25 | 1.25 | 1.25 |
| PEG | 0.2 | 0.2 | 0.2 |
| Mineral Oil | 0.2 | 0.2 | 0.2 |
| Talc coated with Silica Hydrophilic | 0.0 | 10.0 | 0.0 |
| Talc Coated with Silica hydrophobized | 0.0 | 0.0 | 10 |

The talcum powder samples (obtained under examples 2 to 4) above were then kept for storage test and periodically evaluated for its efficacy.

HSGC Measurement

After the 45 days storage period the samples were subjected to HSGC measurement. The results are shown in Table 6 as follows:

TABLE 6

| ELUTION TIME min | Example 2 PEAK AREA | Example 3 PEAK AREA | Example 4 PEAK AREA |
| --- | --- | --- | --- |
| 1.15 | 7899 | 7870 | 7492 |
| 1.42 | 177 | 485 | 530 |
| 1.61 | 313 | 1087 | 1485 |
| 2.00 | 4575 | 7247 | 10819 |
| 2.37 | 966 | 1184 | 1496 |
| 2.71 | 8984 | 20169 | 26485 |
| 2.73 | 366 | 2111 | 406 |
| 3.72 | 633 | 217 | 371 |
| 5.29 | 25089 | 19602 | 23143 |
| 10.72 | 4308 | 4592 | 4792 |
| 11.08 | 37076 | 25733 | 30788 |
| 17.22 | 28533 | 24361 | 27727 |
| 23.58 | 3475 | 2569 | 3082 |
| TOTAL | 126364 | 119585 | 141594 |

The organic compounds in the perfume that have lower elution time i.e. more volatile, less stable components of the blended perfume get more stabilised and show a corresponding increase in the area for talc-silica polymorph samples. The stabilisation is reflected by a marginal increase in the elution time of a few seconds (1 to 3) and the higher HSGC peak areas for examples 3 and 4 compared to example 2. The less HSGC peak area is on account of the perfume loss that has already occurred from the talc sample on account of its lower oil absorption value.

For the hydrophilic silica coated talc the total HSGC area decreases by about 5% while it improves by 12% for the hydrophobized silica coated talc formulation compared to the control. This suggest that perfume retention could be optimised by adjustment of the hydrophilic to hydrophobic character of silica coated talc samples.

These observations suggest that the formulations with talc coated silica preferentially stabilises the more volatile less stable components of the blended perfume. These components are usually responsible for the high notes. However, the total area (GC units) increases on usage of talc coated silica in the formulation, which indicates less losses of perfume.

These results indicate increase in the perfume impact level in the talcum powder formulated with talc silica polymorphs.

Perfumery Evaluation

The talcum powder formulations (Examples 2 to 4) were subjected to storage test and periodically evaluated by the perfumery section for its efficacy. The three formulations were stored for a period of 4 months at 10° C. in a cooling incubator, room temperature i.e., 30° C. and at 45° C. in a humidity chamber. All the samples for the entire storage test period were evaluated to have acceptable fragrance levels.

Flow Property

The flow property of the three samples (Example 2 to 4) are compared below. The weight of powder collected for equivalent shake down from the talcum powder is used as the method. The average of three measurements are used as illustrated in Table 7.

TABLE 7

| Parameter | Example 2 | Example 3 | Example 4 |
| --- | --- | --- | --- |
| Wt of powder collected, g | 0.320 | 1.014 | 0.915 |

The results illustrated in Table 7 above indicates a three fold improvement in flow property.

It is thus possible by the way of the present invention to provide for improved characteristics/benefits of talc by modifying talc in the form of talc coated and/or precipitated with porous material such as herein described and illustrated. In particular the use of talc coated silica in talcum powder formulations is found to be beneficial for perfume stabilisation, enhanced moisture tolerance, subsequent release of perfume, reduced loss of perfume along with improved flow properties. The invention therefore also provides for perceptible benefits of long lasting freshness by way of better retention of perfume and sweat absorption. Importantly the invention is directed further to achieve advantages/beneficial use of talc coated/precipitated porous material such as silica for variety of products including deodorants (for e.g. liquids, gels, aerosols and sticks), fragrances for e.g. after shave gels/lotions, other perfumery products and skin care products for e.g. creams/lotions/gels and facial washes.

EXAMPLE 5

An anhydrous antiperspirant cream was produced having the following formulation:

| Ingredient | % wt |
| --- | --- |
| AZAG (Powder) | 24.0 |
| Castorwax MP80 | 5.0 |
| GE SF1642 (1229-425) | 6.0 |
| Volatile Silicone | 44.0 |
| Non-Volatile Hydrocarbon (Albemarle Silkflo 364NF) | 14.0 |
| Talc coated with silica | 6.0 |
| Fragrance | 1.0 |

The cream was made by adding Silkflo to Volatile Silicone starting the stirrer to half speed and heating to 66° C. The powders were drawn in and mixed for 5 minutes. When addition was complete, the mixture was reheated to 66° C. The waxes were premelted at 80° C. and then added to the main vessel with stirring at full speed. The perfume was added and sheared for 5 minutes at 68 to 70° C.

What is claimed is:

1. A cosmetic talc-containing product comprising:
   (i) a hydrophobic or hydrophilic talc at least partially coated with a porous silica precipitated through acidification onto a wetted talc; and
   (ii) a cosmetic formulation with an active selected from the group consisting of non-coated talc, deodorant, skin care and perfume actives.

2. The cosmetic product according to claim 1 wherein the active is uncoated talc.

3. The cosmetic product according to claim 2 wherein the hydrophilic or hydrophobic talc is present in an amount from 5 to 20% by weight of total talc in the product.

4. The cosmetic product according to claim 1 wherein the active is perfume.

5. The cosmetic product according to claim 1 wherein the skin care active is a volatile silicone.

6. The cosmetic product according to claim 1 wherein the coated talc is a hydrophilic talc.

7. The cosmetic product according to claim 1 wherein the coated talc is a hydrophobic talc.

8. The cosmetic product according to claim 1 wherein particle size of talc which is coated ranges from about 0.01 to 0.03 mm and the coated silica has a particle size ranging from 3 to 6 microns.

9. The cosmetic product according to claim 1 wherein the silica is an amorphous silica.

* * * * *